(12) United States Patent
Nardi et al.

(10) Patent No.: US 8,110,588 B2
(45) Date of Patent: Feb. 7, 2012

(54) 1,2,3-TRIAZOLE DERIVATIVES USEFUL AS MODULATORS OF NICOTINIC ACETYLCHOLINE RECEPTORS

(75) Inventors: Antonio Nardi, Ballerup (DK); Jeppe Kejser Christensen, København N (DK); Dan Peters, Malmö (SE); Gunnar M. Olsen, Smørum (DK); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 12/672,252

(22) PCT Filed: Aug. 6, 2008

(86) PCT No.: PCT/EP2008/060307
§ 371 (c)(1),
(2), (4) Date: Apr. 19, 2010

(87) PCT Pub. No.: WO2009/019278
PCT Pub. Date: Feb. 12, 2009

(65) Prior Publication Data
US 2010/0222398 A1  Sep. 2, 2010

Related U.S. Application Data

(60) Provisional application No. 60/955,081, filed on Aug. 10, 2007.

(30) Foreign Application Priority Data

Aug. 8, 2007  (DK) .................................. 2007 01134

(51) Int. Cl.
*C07D 413/10* (2006.01)
*C07D 249/06* (2006.01)
*A61K 31/4192* (2006.01)
*A61K 31/4245* (2006.01)

(52) U.S. Cl. ......... 514/359; 548/143; 548/255; 514/364
(58) Field of Classification Search .................. 514/359, 514/364; 548/255, 143
See application file for complete search history.

(56) References Cited

U.S. PATENT DOCUMENTS
3,437,663 A  4/1969  Viehe et al.
2005/0020585 A1  1/2005  Cosford et al.

FOREIGN PATENT DOCUMENTS
NL  6 507 886 A  12/1965
WO  WO-03/091226 A1  11/2003
WO  WO-2005/108347 A2  11/2005
WO  WO-2006/071184 A1  7/2006
WO  WO-2009/112459 A1  9/2009
WO  WO 2010/015583 A1  2/2010

OTHER PUBLICATIONS

CAS Registry entry for Registry No. 252654-01-6, entered STN on Jan. 11, 2000.*
Smith et al. J. Org. Chem. 1990, 55, 3351-3362.*
Brown et al., "Characterization of Smith's Nitrene and 1-Phenyl-3-(α-cyano)benzylidenetriazene with Theoretical, NMR, and Flash Photolytic Methods", Journal of Physical Chemistry A, XP-002507239, 1998, vol. 102, pp. 8537-8540.
Smith et al., "The Chemistry of 3-(α-Cyanobenzylidene)-1-phenyltriazenes and Their Conversion to Diarylmaleimides and Phenanthrene-9,10-dicarboximides", Journal of Organic Chemistry, XP-002507240, 1990, vol. 55, pp. 3351-3362.
Alam et al., "Synthesis and Structure-Activity Relationships of 1-Phenyl-1H-1,2,3-triazoles as Selective Insect GABA Receptor Antagonists", Journal of Agricultural and Food Chemistry, XP-002507241, 2006, vol. 54, pp. 1361-1372.
Fuks et al., "Condensation of Alkynylamines with 1,3-Dipolar Compounds, Carbonyl Compounds, and Schiff Bases", Angewandte Chemie International Edition, XP-002507242, vol. 5, No. 6, 1966, p. 585.
Lieber et al., "Synthesis and Isomerization of Substituted 5-Amino-1,2,3-triazoles", Journal of Organic Chemistry, XP-002507243, 1957, vol. 22, pp. 654-662.

* cited by examiner

*Primary Examiner* — Joseph Kosack
*Assistant Examiner* — Matthew Coughlin
(74) *Attorney, Agent, or Firm* — Birch, Stewart, Kolasch & Birch, LLP (57) ABSTRACT

This invention relates to novel 1,2,3-triazole derivatives, which are found to be modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

9 Claims, 2 Drawing Sheets

1,2,3-TRIAZOLE DERIVATIVES USEFUL AS MODULATORS OF NICOTINIC ACETYLCHOLINE RECEPTORS

TECHNICAL FIELD

This invention relates to novel 1,2,3-triazole derivatives, which are found to be modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism.

Smith et al. (Smith P A S, Friar J J, Resemann W & Watson A C; *Journal of Organic Chemistry* 1990 55 (10) 3351-62) describe the chemistry of certain 3-α-cyanobenzylidene)-1-phenyltriazenes and their conversion to diarylmaleimides and phenanthrene-9,10-dicarboximides. However, the 1,2,3-triazole derivatives of the present invention have not been disclosed, and their use as modulators of the nicotinic receptors never suggested.

SUMMARY OF THE INVENTION

The present invention is devoted to the provision novel modulators of the nicotinic receptors, which modulators are useful for the treatment of diseases or disorders related to the cholinergic receptors, and in particular the nicotinic acetylcholine α7 receptor subtype.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides 1,2,3-triazole derivatives of Formula I (I)

a stereoisomer thereof or a mixture of its stereoisomers, or a pharmaceutically acceptable salt thereof, wherein
one of X' and X" represents C; and
the other of X' and X" represents N;
R' and R", independently of each other, represent hydrogen or alkyl;
$R^1$, $R^2$, $R^3$, $R^4$ and $R^5$, independently of each other, represent a substituent selected from the group consisting of hydrogen, alkyl, halo, trifluoromethyl, trifluoromethoxy, cyano, alkoxy, hydroxy, amino, N-(alkyl-carbonyl)-amino, sulfamoyl and oxadiazolyl; and
Y represents an aryl or heteroaryl group selected from phenyl and isoxazolyl.

In a second aspect the invention provides pharmaceutical compositions comprising a therapeutically effective amount of the 1,2,3-triazole derivative of the invention, or a pharmaceutically-acceptable addition salt thereof, together with at least one pharmaceutically-acceptable carrier or diluent.

Viewed from another aspect the invention relates to the use of the 1,2,3-triazole derivative of the invention, or a pharmaceutically-acceptable addition salt thereof, for the manufacture of pharmaceutical compositions/medicaments for the treatment, prevention or alleviation of a disease or a disorder or a condition of a mammal, including a human, which disease, disorder or condition is responsive to modulation of cholinergic receptors.

In yet another aspect the invention provides a method for treatment, prevention or alleviation of diseases, disorders or conditions of a living animal body, including a human, which disorder, disease or condition is responsive to modulation of cholinergic receptors, and which method comprises the step of administering to such a living animal body in need thereof a therapeutically effective amount of the 1,2,3-triazole derivative of the invention.

Other objects of the invention will be apparent to the person skilled in the art from the following detailed description and examples.

DETAILED DISCLOSURE OF THE INVENTION

1,2,3-Triazole Derivatives

In its first aspect the invention provides 1,2,3-triazole derivatives of Formula I (I)

a stereoisomer thereof or a mixture of its stereoisomers, or a pharmaceutically acceptable salt thereof, wherein
one of X' and X" represents C; and
the other of X' and X" represents N;

R' and R", independently of each other, represent hydrogen or alkyl;

$R^1$, $R^2$, $R^3$, $R^4$ and $R^5$, independently of each other, represent a substituent selected from the group consisting of hydrogen, alkyl, halo, trifluoromethyl, trifluoromethoxy, cyano, alkoxy, hydroxy, amino, N-(alkyl-carbonyl)-amino, sulfamoyl and oxadiazolyl; and Y represents an aryl or heteroaryl group selected from phenyl and isoxazolyl.

In a more preferred embodiment the 1,2,3-triazole derivative is a compound represented by Formula Ia (Ia)

a stereoisomer thereof or a mixture of its stereoisomers, or a pharmaceutically acceptable salt thereof, wherein one of X' and X" represents C; and the other of X' and X" represents N;

R' and R", independently of each other, represent hydrogen or alkyl;

$R^1$, $R^2$, $R^3$ and $R^4$, independently of each other, represent a substituent selected from the group consisting of hydrogen, alkyl, halo, trifluoromethyl, cyano, alkoxy and hydroxy; and Y represents an aryl or heteroaryl group selected from phenyl and isoxazolyl.

In another more preferred embodiment the 1,2,3-triazole derivative of the invention is a compound represented by Formula Ib (Ib)

a stereoisomer thereof or a mixture of its stereoisomers, or a pharmaceutically acceptable salt thereof, wherein R', R", $R^1$, $R^2$, $R^3$, $R^4$, $R^5$ and Y are as defined above.

In a third more preferred embodiment the 1,2,3-triazole derivative of the invention is a compound represented by Formula Ic (Ic)

a stereoisomer thereof or a mixture of its stereoisomers, or a pharmaceutically acceptable salt thereof, wherein R', R", $R^1$, $R^2$, $R^3$, $R^4$, $R^5$ and Y are as defined above.

In a preferred embodiment the 1,2,3-triazole derivative of the invention is a compound of Formula I, or a pharmaceutically acceptable salt thereof, wherein one of X' and X" represents C; and the other of X' and X" represents N.

In a more preferred embodiment X' represents C and X" represents N.

In another more preferred embodiment X' represents N and X" represents C.

In another preferred embodiment the 1,2,3-triazole derivative of the invention is a compound of Formula I, or a pharmaceutically acceptable salt thereof, wherein R' and R", independently of each other, represent hydrogen or alkyl.

In a more preferred embodiment R' and R" both represent hydrogen.

In another more preferred embodiment R' and R" both represent alkyl.

In a third preferred embodiment the 1,2,3-triazole derivative of the invention is a compound of Formula I, or a pharmaceutically acceptable salt thereof, wherein $R^1$, $R^2$, $R^3$, $R^4$ and $R^5$, independently of each other, represent a substituent selected from the group consisting of hydrogen, alkyl, halo, trifluoromethyl, trifluoromethoxy, cyano, alkoxy, hydroxy, amino, N-(alkyl-carbonyl)-amino, sulfamoyl and oxadiazolyl.

In a more preferred embodiment $R^1$, $R^2$, $R^3$ and $R^4$, independently of each other, represent a substituent selected from the group consisting of hydrogen, alkyl, halo, trifluoromethyl, cyano, alkoxy and hydroxy; and $R^5$ represents hydrogen.

In another more preferred embodiment $R^1$, $R^2$, $R^3$ and $R^4$, independently of each other, represent a substituent selected from the group consisting of hydrogen, alkyl, halo, trifluoromethyl, alkoxy and hydroxy, and $R^5$ represents hydrogen.

In an even more preferred embodiment one of $R^1$ and $R^2$ represents hydrogen; and the other of $R^1$ and $R^2$ represents halo, trifluoromethyl, cyano, alkoxy, hydroxy, amino, N-(alkyl-carbonyl)-amino, sulfamoyl or oxadiazolyl.

In another even more preferred embodiment one of $R^1$ and $R^2$ represents hydrogen; and the other of $R^1$ and $R^2$ represents alkoxy, and in particular methoxy, or hydroxy.

In a third even more preferred embodiment one of $R^1$ and $R^2$ represents hydrogen; and the other of $R^1$ and $R^2$ represents alkoxy, and in particular methoxy.

In a fourth even more preferred embodiment one of $R^1$ and $R^2$ represents hydrogen; and the other of $R^1$ and $R^2$ represents hydroxy.

In a fifth even more preferred embodiment one of $R^1$ and $R^2$ represents hydrogen; and the other of $R^1$ and $R^2$ represents halo, trifluoromethyl, cyano, amino, N-(alkyl-carbonyl)-amino, sulfamoyl or oxadiazolyl.

In a sixth even more preferred embodiment one of $R^1$ and $R^2$ represents hydrogen; and the other of $R^1$ and $R^2$ represents halo.

In a seventh even more preferred embodiment one of $R^1$ and $R^2$ represents hydrogen; and the other of $R^1$ and $R^2$ represents trifluoromethyl.

In an eighth even more preferred embodiment one of $R^1$ and $R^2$ represents hydrogen; and the other of $R^1$ and $R^2$ represents cyano.

In a ninth even more preferred embodiment one of $R^1$ and $R^2$ represents hydrogen; and the other of $R^1$ and $R^2$ represents amino.

In a tenth even more preferred embodiment one of $R^1$ and $R^2$ represents hydrogen; and the other of $R^1$ and $R^2$ represents N-(alkyl-carbonyl)-amino, and in particular N-methyl-carbonyl-amino.

In an eleventh even more preferred embodiment one of $R^1$ and $R^2$ represents hydrogen; and the other of $R^1$ and $R^2$ represents sulfamoyl.

In a twelfth even more preferred embodiment one of $R^1$ and $R^2$ represents hydrogen; and the other of $R^1$ and $R^2$ represents oxadiazolyl, and in particular [1,3,4]oxadiazol-2-yl.

In a thirteenth even more preferred embodiment one of $R^1$ and $R^2$ represents halo, and in particular chloro; and the other of $R^1$ and $R^2$ represents hydroxy; and $R^5$ represents hydrogen.

In a fourteenth even more preferred embodiment one of $R^1$ and $R^2$ represents halo, and in particular chloro; and the other of $R^1$ and $R^2$ represents alkoxy, and in particular methoxy; and $R^5$ represents hydrogen.

In yet another even more preferred embodiment of $R^3$ and $R^4$ represents halo, and in particular fluoro or chloro; and the other of $R^3$ and $R^4$ represents halo, and in particular fluoro or chloro, or trifluoromethyl; and $R^5$ represents hydrogen.

In another even more preferred embodiment one of $R^3$ and $R^4$ represents halo, and in particular fluoro or chloro; and the other of $R^3$ and $R^4$ represents halo, and in particular fluoro or chloro; and $R^5$ represents hydrogen.

In a third even more preferred embodiment one of $R^3$ and $R^4$ represents halo, and in particular fluoro or chloro; and the other of $R^3$ and $R^4$ represents trifluoromethyl; and $R^5$ represents hydrogen.

In a fourth even more preferred embodiment one of $R^3$ and $R^4$ represents hydrogen; and the other of $R^3$ and $R^4$ represents alkyl, and in particular methyl; and $R^5$ represents hydrogen.

In a fifth even more preferred embodiment one of $R^3$ and $R^4$ represents hydrogen; and the other of $R^3$ and $R^4$ represents alkyl, and in particular methyl; and $R^5$ represents hydrogen.

In a sixth even more preferred embodiment $R^3$, $R^4$ and $R^5$, independently of each other, represent halo, and in particular chloro, or trifluoromethyl.

In a seventh even more preferred embodiment $R^3$, $R^4$ and $R^5$, independently of each other, represent halo, and in particular chloro or iodo.

In an eighth even more preferred embodiment $R^3$ and $R^4$ both represent chloro; and $R^5$ represents iodo.

In a fourth preferred embodiment the 1,2,3-triazole derivative of the invention is a compound of Formula I, or a pharmaceutically acceptable salt thereof, wherein Y represents an aryl or heteroaryl group selected from phenyl and isoxazolyl.

In a more preferred embodiment Y represents phenyl.

In another more preferred embodiment Y represents isoxazolyl, and in particular isoxazol-3-yl.

In a fifth preferred embodiment the 1,2,3-triazole derivative of the invention is a compound of Formula I, or a pharmaceutically acceptable salt thereof, wherein
one of $R^1$ and $R^2$ represents hydrogen; and the other of $R^1$ and $R^2$ represents alkoxy, and in particular methoxy;
one of $R^3$ and $R^4$ represents hydrogen; and the other of $R^3$ and $R^4$ represents alkyl, and in particular methyl; and $R^5$ represents hydrogen; and
Y represents isoxazolyl, and in particular isoxazol-3-yl.

In a most preferred embodiment the 1,2,3-triazole derivative of the invention is
3-(2,4-Dichloro-phenyl)-5-(4-methoxy-phenyl)-3H-[1,2,3]triazol-4-ylamine;
5-(5-Chloro-2-methoxy-phenyl)-3-(2-chloro-4-trifluoromethyl-phenyl)-3H-[1,2,3]triazol-4-ylamine;
3-(2-Chloro-4-trifluoromethyl-phenyl)-5-(4-methoxy-phenyl)-3H-[1,2,3]triazol-4-ylamine;
5-(5-Chloro-2-methoxy-phenyl)-3-(2,4-dichloro-phenyl)-3H-[1,2,3]triazol-4-ylamine;
3-(2-Chloro-4-fluoro-phenyl)-5-(4-methoxy-phenyl)-3H-[1,2,3]triazol-4-ylamine;
5-(2,4-Dichloro-phenyl)-3-(4-methoxy-phenyl)-3H-[1,2,3]triazol-4-ylamine;
5-(4-Methoxy-phenyl)-3-(5-methyl-isoxazol-3-yl)-3H-[1,2,3]triazol-4-yl amine;
2-[5-Amino-1-(2,4-dichloro-phenyl)-1H-[1,2,3]triazol-4-yl]-4-chloro-phenol; or
2-[5-Amino-1-(2-chloro-4-trifluoromethyl-phenyl)-1H-[1,2,3]triazol-4-yl]-4-chloro-phenol;
3-(2-Fluoro-4-trifluoromethyl-phenyl)-5-(4-[1,3,4]oxadiazol-2-yl-phenyl)-3H-[1,2,3]triazol-4-ylamine;
N-{4-[5-Amino-1-(2-fluoro-4-trifluoromethyl-phenyl)-1H-[1,2,3]triazol-4-yl]-phenyl}-acetamide;
5-(4-Amino-phenyl)-3-(2-fluoro-4-trifluoromethyl-phenyl)-3H-[1,2,3]triazol-4-ylamine;
4-[5-Amino-4-(2-fluoro-4-trifluoromethyl-phenyl)-[1,2,3]triazol-1-yl]-benzenesulfonamide;
3-(2-Fluoro-4-trifluoromethyl-phenyl)-5-(4-methoxy-phenyl)-3H-[1,2,3]triazol-4-ylamine;
4-[5-Amino-1-(2-fluoro-4-trifluoromethyl-phenyl)-1H-[1,2,3]triazol-4-yl]-phenol;
5-(2-Fluoro-4-trifluoromethyl-phenyl)-3-(4-methoxy-phenyl)-3H-[1,2,3]triazol-4-ylamine;
4-[5-Amino-4-(2-fluoro-4-trifluoromethyl-phenyl)-[1,2,3]triazol-1-yl]-phenol;
5-(4-Chloro-phenyl)-3-(2-fluoro-4-trifluoromethyl-phenyl)-3H-[1,2,3]triazol-4-ylamine;
3-(2-Fluoro-4-trifluoromethyl-phenyl)-5-(4-trifluoromethoxy-phenyl)-3H-[1,2,3]triazol-4-ylamine;
4-[5-Amino-1-(2,4-dichloro-phenyl)-1H-[1,2,3]triazol-4-yl]-benzonitrile;
4-[5-Amino-1-(2-chloro-4-trifluoromethyl-phenyl)-1H-[1,2,3]triazol-4-yl]-phenol;
3-(2,4-Dichloro-6-iodo-phenyl)-5-(4-methoxy-phenyl)-3H-[1,2,3]triazol-4-ylamine;
5-(4-Chloro-2-trifluoromethyl-phenyl)-3-(4-methoxy-phenyl)-3H-[1,2,3]triazol-4-ylamine;
5-(2,4-Difluoro-phenyl)-3-(4-methoxy-phenyl)-3H-[1,2,3]triazol-4-ylamine;
5-(2-Chloro-4-fluoro-phenyl)-3-(4-methoxy-phenyl)-3H-[1,2,3]triazol-4-ylamine;
5-(3,4-Dichloro-phenyl)-3-(4-methoxy-phenyl)-3H-[1,2,3]triazol-4-ylamine; or
5-(4-Chloro-2-fluoro-phenyl)-3-(4-methoxy-phenyl)-3H-[1,2,3]triazol-4-ylamine;
a stereoisomer thereof or a mixture of its stereoisomers, or a pharmaceutically acceptable salt thereof.

Any combination of two or more of the embodiments described herein is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkoxy group designates an "alkyl-O—" group, wherein alkyl is as defined above. Examples of preferred alkoxy groups of the invention include methoxy and ethoxy.

In the context of this invention Y represents an aryl or heteroaryl group selected from phenyl and isoxazolyl. The isoxazolyl group may in particular be isoxazol-3-yl, isoxazol-4-yl or isoxazol-5-yl.

Pharmaceutically Acceptable Salts

The 1,2,3-triazole derivative of the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a 1,2,3-triazole derivative of the invention include alkali metal salts, such as the sodium salt of a compound of the invention containing a carboxy group.

Steric Isomers

It will be appreciated by those skilled in the art that the 1,2,3-triazole derivatives of the present invention may exist in different stereo isomeric forms, including enantiomers, diastereomers, as well as geometric isomers (cis-trans isomers). The invention includes all such stereoisomers and any mixtures thereof including racemic mixtures.

Racemic forms can be resolved into the optical antipodes by known methods and techniques. One way of separating the enantiomeric compounds (including enantiomeric intermediates) is—in the case the compound being a chiral acid by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphor-sulphonate) salts for example.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optically active starting materials or intermediates.

Methods of Producing 1,2,3-Triazole Derivatives

The 1,2,3-triazole derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel modulators of the nicotinic receptors, which modulators are useful for the treatment of diseases or disorders related to the cholinergic receptors, and in particular the nicotinic acetylcholine receptor (nAChR). Preferred compounds of the invention show a pronounced nicotinic acetylcholine α7 receptor subtype selectivity.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In a preferred embodiment the disease, disorder or condition contemplated according to the invention, and responsive to modulation of nicotinic acetylcholine receptors is anxiety, a cognitive disorder, a learning deficit, a memory deficit or dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, psychosis, schizophrenia, obsessive compulsive disorders (OCD), panic disorders, an eating disorder including anorexia nervosa, bulimia and obesity, narcolepsy, nociception, AIDS-dementia, senile dementia, periferic neuropathy, autism, dyslexia, tardive dyskinesia, hyperkinesia, epilepsy, post-traumatic syndrome, social phobia, a sleeping disorder, pseudo dementia, Ganser's syndrome, pre-menstrual syndrome, late luteal phase syndrome, chronic fatigue syndrome, mutism, trichotillomania, jet-lag, hypertension, cardiac arrhythmias, a smooth muscle contraction disorder including convulsive disorders, angina pectoris, premature labour, convulsions, diarrhoea, asthma, epilepsy, tardive dyskinesia, hyperkinesia, premature ejaculation and erectile difficulty, an endocrine system disorder including thyrotoxicosis and pheochromocytoma, a neurodegenerative disorder, including transient anoxia and induced neuro-degeneration, pain, mild, moderate or severe pain, acute pain, chronic pain, pain of recurrent character, neuropathic pain, pain caused by migraine, postoperative pain, phantom limb pain, neuropathic pain, chronic headache, central pain, pain related to diabetic neuropathy, to post therapeutic neuralgia or to peripheral nerve injury, an inflammatory disorder, including an inflammatory skin disorder, acne, rosacea, Chron's disease, inflammatory bowel disease, ulcerative colitis and diarrhoea, a disorder associated withdrawal symptoms caused by termination of use of addictive substances, including nicotine withdrawal symptoms, opioid withdrawal symptoms including heroin, cocaine and morphine, benzodiazepine withdrawal symptoms including benzodiazepine-like drugs and alcohol.

In a more preferred embodiment the disease, disorder or condition responsive to modulation of nicotinic acetylcholine receptors is a cognitive disorder, psychosis, schizophrenia or depression.

In another more preferred embodiment the disease, disorder or condition responsive to modulation of nicotinic acetylcholine receptors is associated with smooth muscle contractions, including convulsive disorders, angina pectoris, premature labour, convulsions, diarrhoea, asthma, epilepsy, tardive dyskinesia, hyperkinesia, premature ejaculation and erectile difficulty.

In still another more preferred embodiment the disease, disorder or condition responsive to modulation of nicotinic acetylcholine receptors is related to the endocrine system, such as thyrotoxicosis and pheochromocytoma.

In yet another more preferred embodiment the disease, disorder or condition responsive to modulation of nicotinic acetylcholine receptors is a neurodegenerative disorder including transient anoxia and induced neuro-degeneration.

In a further more preferred embodiment the disease, disorder or condition responsive to modulation of nicotinic acetylcholine receptors is pain, including mild, moderate or even severe pain of acute, chronic or recurrent character, as well as pain caused by migraine, postoperative pain, and phantom limb pain. The pain may in particular be neuropathic pain, chronic headache, central pain, pain related to diabetic neuropathy, to post therapeutic neuralgia, or to peripheral nerve injury.

In a further more preferred embodiment the disease, disorder or condition responsive to modulation of nicotinic acetylcholine receptors is an inflammatory skin disorder such as acne and rosacea, Chron's disease, inflammatory bowel disease, ulcerative colitis, and diarrhoea.

Finally the compounds of the invention may be useful for the treatment of abuse liability and withdrawal symptoms caused by termination of use of addictive substances. Such addictive substances include nicotine containing products such as tobacco, opioids such as heroin, cocaine, morphine and cannabis, benzodiazepines and benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

Pharmaceutical Compositions

In another aspect the invention provides novel pharmaceutical compositions comprising a therapeutically effective amount of 1,2,3-triazole derivative of the invention.

While a 1,2,3-triazole derivative of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 1,2,3-triazole derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The 1,2,3-triazole derivatives of the present invention are valuable nicotinic receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors, and which method comprises administering to such a living animal body, including a human, in need thereof an effective amount of a 1,2,3-triazole derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

BRIEF DESCRIPTION OF THE DRAWING

The present invention is further illustrated by reference to the accompanying drawing, in which FIGS. 1A and 1B show the modulatory effect of Compound 1 (i.e. 3-(2,4-dichlorophenyl)-5-(4-methoxy-phenyl)-3H-[1,2,3]triazol-4-ylamine); and FIGS. 2A and 2B show the modulatory effect of Compound 3 (i.e. 3-(2-chloro-4-trifluoromethyl-phenyl)-5-(4-methoxy-phenyl)-3H-[1,2,3]triazol-4-ylamine) on acetylcholine currents induced in nAChR α7 receptors expressed in *Xenopus* oocytes:

EXAMPLES

The invention is further illustrated with reference to the following examples, which are not intended to be in any way limiting to the scope of the invention as claimed.

Example 1

Preparatory Example

General Experimental Procedure

Chemical synthesis of the 1,2,3-triazole derivatives of the invention is envisioned by the use of suitably-substituted arylazides. These were prepared via nucleophilic aromatic substitution from the correspondent commercial amines, through the adduct formation of the azido ion on the diazonium salt intermediates and the following collapse of the adduct with loss of nitrogen. Resulting arylazides finally undergo a base-catalysed and regiospecific condensation with proper activated methylenic compounds, i.e. (substituted or not) commercial phenylacetonitriles. In presence of methyl ether substituent(s), ether cleavage follows, upon mild nucleophilic substitution with the Lewis acid boron tribromide.

3-(2,4-Dichloro-phenyl)-5-(4-methoxy-phenyl)-3H-[1,2,3]triazol-4-ylamine (1)

To an ice-cooled and stirred mixture of 1-azido-2,4-dichloro-benzene (0.400 g, 1 eq) and commercial (4-methoxy-phenyl)-acetonitrile (0.376 g, 1.2 eq) in ethanol (3 ml) kept under nitrogen, a solution of sodium methoxide (0.172 g, 1.5 eq) in ethanol (2 ml) is added drop-wise (15 min). After the addition, the reaction mixture is allowed to reach room temperature spontaneously and stirring is then continued overnight at room temperature. The resulting reaction mixture is diluted with ethyl acetate (25 ml), washed with water (2×25 ml), dried over $MgSO_4$ and evaporated to dryness. The yellow semisolid residue (0.750 g) is purified by crystallization from a mixture of dichloromethane and hexane (1:1), to afford the title compound as white solid (0.315 g, 44% yield). M.p. 149.2-150.7° C.

5-(5-Chloro-2-methoxy-phenyl)-3-(2-chloro-4-trifluoromethyl-phenyl)-3H-[1,2,3]triazol-4-ylamine (2)

To an ice-cooled and stirred mixture of 1-azido-2-chloro-4-trifluoromethyl-benzene (0.500 g, 1 eq) and commercial (5-chloro-2-methoxy-phenyl)-acetonitrile (0.492 g, 1.2 eq) in ethanol (4 ml) kept under nitrogen, a solution of sodium methoxide (0.183 g, 1.5 eq) in ethanol (2 ml) is added drop-wise (15 min). After the addition, the reaction mixture is allowed to reach room temperature spontaneously and stirring is then continued overnight at room temperature. The resulting reaction mixture is diluted with ethyl acetate (25 ml), washed with water (2×25 ml), dried over $MgSO_4$ and evaporated to dryness. The yellow solid residue (0.610 g) is purified by crystallization from a mixture of dichloromethane and hexane (1:1), to afford the title compound as white solid (0.450 g, 50% yield). M.p. 152.8-153.3° C.

3-(2-Chloro-4-trifluoromethyl-phenyl)-5-(4-methoxy-phenyl)-3H-[1,2,3]triazol-4-ylamine (3)

To an ice-cooled and stirred mixture of 1-azido-2-chloro-4-trifluoromethyl-benzene (1.00 g, 1 eq) and commercial (4-methoxy-phenyl)-acetonitrile (0.797 g, 1.2 eq) in ethanol (10 ml) kept under nitrogen, a solution of sodium methoxide (0.366 g, 1.5 eq) in ethanol (10 ml) is added drop-wise (20 min). After the addition, the reaction mixture is allowed to reach room temperature spontaneously and stirring is then continued overnight at room temperature. The resulting reaction mixture is diluted with ethyl acetate (40 ml), washed with water (2×50 ml), dried over $MgSO_4$ and evaporated to dryness. The yellow solid residue (1.20 g) is purified by flash chromatography using 60-120 mesh silica gel and eluting with 15% ethylacetate in hexane, to afford the title compound as a white solid (0.324 g, 30% yield). M.p. 130.0-130.7° C.

5-(5-Chloro-2-methoxy-phenyl)-3-(2,4-dichloro-phenyl)-3H-[1,2,3]triazol-4-ylamine (4)

To an ice-cooled and stirred mixture of 1-azido-2,4-dichloro-benzene (0.9 g, 1 eq) and commercial (5-chloro-2-methoxy-phenyl)-acetonitrile (1.04 g, 1.2 eq) in ethanol (10 ml) kept under nitrogen, a solution of sodium methoxide (0.388 g, 1.5 eq) in ethanol (10 ml) is added drop-wise (20 min). After the addition, the reaction mixture is allowed to reach room temperature spontaneously and stirring is then continued overnight at room temperature. The resulting reaction mixture is diluted with ethyl acetate (40 ml), washed with water (2×50 ml), dried over $MgSO_4$ and evaporated to dryness. The yellow solid residue (0.820 g) is purified by crystallization from a mixture of dichloromethane and hexane (1:1), to afford the title compound as white solid (0.480 g, 28% yield). M.p. 153.5-154.7° C.

3-(2-Chloro-4-fluoro-phenyl)-5-(4-methoxy-phenyl)-3H-[1,2,3]triazol-4-ylamine (5)

To an ice-cooled and stirred mixture of 1-azido-2-chloro-4-fluoro-benzene (0.300 g, 1 eq) and commercial (4-methoxy-phenyl)-acetonitrile (0.309 g, 1.2 eq) in ethanol (5 ml) kept under nitrogen, a solution of sodium methoxide (0.142 g, 1.5 eq) in ethanol (5 ml) is added drop-wise (15 min). After the addition, the reaction mixture is allowed to reach room temperature spontaneously and stirring is then continued overnight at room temperature. The resulting reaction mixture is diluted with ethyl acetate (20 ml), washed with water (2×25 ml), dried over $MgSO_4$ and evaporated to dryness. The yellow semisolid residue (~0.500 g) is purified by flash chromatography using 60-120 mesh silica gel and eluting with 20% ethylacetate in hexane, to afford the title compound as a white solid (0.190 g, 34% yield). M.p. 136.3-141.2° C.

5-(2,4-Dichloro-phenyl)-3-(4-methoxy-phenyl)-3H-[1,2,3]triazol-4-ylamine (6)

To an ice-cooled and stirred mixture of 1-azido-4-methoxy-benzene (0.750 g, 1 eq) and commercial (2,4-dichlorophenyl)-acetonitrile (1.12 g, 1.2 eq) in ethanol (10 ml) kept under nitrogen, a solution of sodium methoxide (0.408 g, 1.5 eq) in ethanol (10 ml) is added drop-wise (25 min). After the addition, the reaction mixture is allowed to reach room temperature spontaneously and stirring is then continued overnight at room temperature. The resulting reaction mixture is diluted with ethyl acetate (40 ml), washed with water (2×50 ml), dried over MgSO$_4$ and evaporated to dryness. The yellow semisolid residue (0.842 g) is purified by flash chromatography using 60-120 mesh silica gel and eluting with 15% ethylacetate in hexane, to afford the title compound as a white solid (0.428 g, 24% yield). M.p. 154.6-163.9° C.

5-(4-Methoxy-phenyl)-3-(5-methyl-isoxazol-3-yl)-3H-[1,2,3]triazol-4-yl amine (7)

To an ice-cooled and stirred mixture of 3-azido-5-methyl-isoxazole (0.5 g, 1 eq) and commercial (4-methoxy-phenyl)-acetonitrile (0.712 g, 1.2 eq) in ethanol (10 ml) kept under nitrogen, a solution of sodium methoxide (0.327 g, 1.5 eq) in ethanol (10 ml) is added drop-wise (15 min). After the addition, the reaction mixture is allowed to reach room temperature spontaneously and stirring is then continued overnight at room temperature. The resulting reaction mixture is diluted with ethyl acetate (40 ml), washed with water (2×50 ml), dried over MgSO$_4$ and evaporated to dryness. The yellow semisolid residue (~0.900 g) is purified by flash chromatography using 60-120 mesh silica gel and eluting with 20% ethylacetate in hexane, to afford the title compound as a white solid (0.120 g, 11% yield). M.p. 136.3-141.2° C.

2-[5-Amino-1-(2,4-dichloro-phenyl)-1H-[1,2,3]triazol-4-yl]-4-chloro-phenol (8)

To a stirred solution of 5-(5-Chloro-2-methoxy-phenyl)-3-(2,4-dichloro-phenyl)-3H-[1,2,3]triazol-4-ylamine (previously described as Compound 4) (0.3 g, 1 eq) in dry dichloromethane (5 ml), cooled to 0° C. and a nitrogen flow, a solution of boron tribromide (0.15 ml, 2 eq) in 5 ml of dry dichloromethane is added drop-wise. Stirring is continued for 1 hour at 0° C. and one hour at room temperature. The resulting mixture is cooled again in an ice-salt bath and the reagent is decomposed upon treatment with methanol (5 ml) followed by water (5 ml). The organic layer is washed again with (8 ml) water, dried over MgSO$_4$ and evaporated in vacuo, to give a crude solid residue (~0.250 g) which is purified by flash chromatography using 60-120 mesh silica gel and eluting with 15% ethylacetate in hexane, to afford the title compound as purple solid (0.075 g, 37% yield). M.p. 131.3-135.6° C.

2-[5-Amino-1-(2-chloro-4-trifluoromethyl-phenyl)-1H-[1,2,3]triazol-4-yl]-4-chloro-phenol (9)

To a stirred solution of 5-(5-Chloro-2-methoxy-phenyl)-3-(2-chloro-4-trifluoromethyl-phenyl)-3H-[1,2,3]triazol-4-ylamine (previously described as Compound 5) (0.3 g, 1 eq) in dry dichloromethane (5 ml), cooled to 0° C. and a nitrogen flow, a solution of boron tribromide (0.15 ml, 2 eq) in 5 ml of dry dichloromethane is added drop-wise. Stirring is continued for 1 hour at 0° C. and one hour at room temperature. The resulting mixture is cooled again in an ice-salt bath and the reagent is decomposed upon treatment with methanol (5 ml) followed by water (5 ml). The organic layer is washed again with (8 ml) water, dried over MgSO$_4$ and evaporated in vacuo, to give a crude solid residue (~0.200 g) which is purified by crystallization from dichloromethane, to afford the title compound as a purple solid (0.075 g, 37% yield). M.p. 74.5-77.5° C.

3-(2-Fluoro-4-trifluoromethyl-phenyl)-5-(4-[1,3,4]oxadiazol-2-yl-phenyl)-3H-[1,2,3]triazol-4-ylamine (10)

To a stirred and ice-cooled solution of sodium methoxide (0.158 g, 2.9252 mmol) in methanol (25 ml), commercial 2-[4-(1,3,4-oxadiazol-2-yl)phenyl]acetonitrile (0.430 g, 2.3401 mmol) and 1-azido-2-fluoro-4-trifluoromethyl-benzene (0.400 g, 1.9501 mmol) are added under a nitrogen atmosphere. The reaction mixture is kept at 0° C. for 1 h, and then allowed to attain spontaneously room temperature overnight. The reaction mixture is concentrated, added water (30 ml), and extracted with ethylacetate (3×100 ml). The combined organic layers are dried over MgSO$_4$, filtered and evaporated, to afford a pink solid (0.74 g, 97% mass balance). The crude residue is purified by column chromatography over silica gel (230-400 mesh), eluting with 50% ethylacetate in petroleum ether, to obtain the title compound as a yellow solid (0.280 g, 37% yield). M.p. 184.6-186.1° C. LC-ESI-HRMS of [M+H]+ shows 391.0927 Da. Calc. 391.093046 Da, dev. −0.9 ppm.

N-{4-[5-Amino-1-(2-fluoro-4-trifluoromethyl-phenyl)-1H-[1,2,3]triazol-4-yl]-phenyl}-acetamide (11)

To a stirred and ice-cooled solution of potassium tert-butoxide (0.432 g, 3.6566 mmol) in tert-butanol (15 ml), commercial 4-acetamidophenylacetonitrile (0.5096 g, 2.9252 mmol) and 1-azido-2-fluoro-4-trifluoromethyl-benzene (0.500 g, 2.4377 mmol) are added under a nitrogen atmosphere and the reaction mixture is allowed to attain spontaneously room temperature (1 h) and finally refluxed for 6 h. The resulting reaction mixture is concentrated, added water, and extracted with ethylacetate (3×100 ml). The combined organic layers are dried over MgSO$_4$, filtered and evaporated, to afford a dark brown gummy material (0.900 g, 97% mass balance). The crude residue is purified by column chromatography over silica gel (230-400 mesh), eluting with 50% ethylacetate in petroleum ether, to obtain the title compound as a light yellow solid (0.270 g, 30% yield). M.p. 114.8-116.2° C. LC-ESI-HRMS of [M+H]+ shows 380.1125 Da. Calc. 380.113447 Da, dev. −2.5 ppm.

5-(4-Amino-phenyl)-3-(2-fluoro-4-trifluoromethyl-phenyl)-3H-[1,2,3]triazol-4-ylamine (12)

To a stirred and ice-cooled solution of potassium tert-butoxide (1.728 g, 14.626 mmol) in tert-butanol (50 ml), commercial 4-aminophenylacetonitrile (1.418 g, 10.7258 mmol) and 1-azido-2-fluoro-4-trifluoromethyl-benzene (2.000 g, 9.7507 mmol) are added under a nitrogen atmosphere and the reaction mixture is allowed to attain spontaneously room temperature (1 h) and finally refluxed for 6 h. The resulting reaction mixture is concentrated, added water, and extracted with ethylacetate (3×100 ml). The combined organic layers are dried over MgSO$_4$, filtered and evaporated, to afford a dark brown gummy material (3.289 g, 100% mass balance). The crude residue is purified by column chromatography over silica gel (230-400 mesh), eluting with 25% ethylacetate in petroleum ether, to obtain the title compound as a light yellow solid (0.700 g, 21% yield). M.p. 163.6-165.0° C. LC-ESI-HRMS of [M+H]+ shows 338.1021 Da. Calc. 338.102882 Da, dev. –2.3 ppm.

4-[5-Amino-4-(2-fluoro-4-trifluoromethyl-phenyl)-[1,2,3]triazol-1-yl]-benzenesulfonamide (13)

To a stirred and ice-cooled solution of 2-fluoro-4-(trifluoromethyl)phenyl acetonitrile (1.066 g, 5.2471 mmol) and 4-azido-benzenesulfonamide (0.800 g, 4.0362 mmol) in methanol (50 ml), sodium methoxide (0.3271 g, 6.0543 mmol) is added portion wise and the mixture is allowed to attain room temperature spontaneously and stirred for additional 24 hours at this temperature. The reaction mixture is concentrated, water (10 ml) is added and extracted with ethyl acetate (3×80 ml). The combined organic layers are washed with brine (15 ml), dried over MgSO$_4$, filtered and concentrated to afford an off-white solid (1.61 g, ~99% yield, 97.7% pure at HPLC). M.p. 183.8-185.2° C. LC-ESI-HRMS of [M+H]+ shows 402.0638 Da. Calc. 402.064783 Da, dev. –2.4 ppm.

3-(2-Fluoro-4-trifluoromethyl-phenyl)-5-(4-methoxy-phenyl)-3H-[1,2,3]triazol-4-ylamine (14)

To a stirred and ice-cooled solution of sodium methoxide (1.659 g, 30.7146 mmol) in methanol (50 ml), 4-methoxyphenylacetonitrile (3.728 g, 24.5717 mmol) and 1-azido-2-fluoro-4-trifluoromethyl-benzene (4.200 g, 20.4764 mmol) are added portion wise and the mixture is allowed attain room temperature spontaneously and refluxed overnight. The resulting reaction mixture is concentrated, added water, and extracted with chloroform (3×100 mL). The combined organic layers are dried over MgSO$_4$, filtered and concentrated to afford a brownish gummy material (5.900 g, 82% mass balance). The crude residue is purified by column chromatography over silica gel (230-400 mesh), eluting with 15% ethylacetate in hexane, to obtain the title compound as a grey solid (0.120 g, 1.5% yield). A major impurity isolated and characterized is 5-(4-methoxy-phenyl)-3-(2-methoxy-4-trifluoromethyl-phenyl)-3H-[1,2,3]triazol-4-ylamine (2.400 g, ~33% yield).

4-[5-Amino-1-(2-fluoro-4-trifluoromethyl-phenyl)-1H-[1,2,3]triazol-4-yl]-phenol (15)

To a stirred solution of 3-(2-fluoro-4-trifluoromethyl-phenyl)-5-(4-methoxy-phenyl)-3H-[1,2,3]triazol-4-ylamine (14) (0.400 g, 1.1354 mmol) in anhydrous dichloromethane (25 ml), cooled to –78° C. and under a nitrogen flow, a solution of boron tribromide (1.991 g, ~0.75 ml, 7.9478 mmol) in 5 ml of anhydrous dichloromethane is added drop-wise. The mixture is allowed to reach room temperature spontaneously overnight and it is then cooled again in an ice-salt bath and the excess of the reagent is decomposed upon dropwise addition of 10 ml of methanol and 10 ml of water. After 5 min stirring, 10% sodium hydroxide solution (10 ml) is added and the aqueous layer, once separated, is acidified with 10% hydrochloric acid solution and extracted with chloroform (3×70 ml). The combined organic layers are dried over MgSO$_4$, filtered and evaporated to afford a solid residue (0.350 g). This is purified by column chromatography over silica gel (60-120 mesh) eluting with 16% ethyl acetate in hexane (0.150 g, 40% yield). M.p. 163.5-165.2° C. LC-ESI-HRMS of [M+H]+ shows 339.0853 Da. Calc. 339.086898 Da, dev. –4.7 ppm.

5-(2-Fluoro-4-trifluoromethyl-phenyl)-3-(4-methoxy-phenyl)-3H-[1,2,3]triazol-4-ylamine (16)

To an ice-cooled solution of 1-azido-4-methoxy-benzene (0.450 g, 3.0171 mmol) and commercial 2-fluoro-4-(trifluoromethyl)phenyl acetonitrile (0.736 g, 3.6205 mmol) in absolute ethanol (10 ml) and under a nitrogen flow, sodium methoxide (0.2445 g, 4.5257 mmol) in absolute ethanol (5 ml) is added drop-wise and the resulting mixture is allowed to attain room temperature spontaneously overnight. The reaction mixture is evaporated and the solid residue is dissolved in dichloromethane (80 ml) and the organic solution is washed with water (60 ml), brine (60 ml), dried over MgSO$_4$, filtered and evaporated (~1 g). This crude residue is purified by crystallization from a mixture of dichloromethane and petroleum ether, to afford the title compound as a yellow solid (0.570 g, 53% yield). M.p. 164.6-165.5° C. LC-ESI-HRMS of [M+H]+ shows 353.1028 Da. Calc. 353.102548 Da, dev. 0.7 ppm.

4-[5-Amino-4-(2-fluoro-4-trifluoromethyl-phenyl)-[1,2,3]triazol-1-yl]-phenol (17)

To a stirred solution of 5-(2-fluoro-4-trifluoromethyl-phenyl)-3-(4-methoxy-phenyl)-3H-[1,2,3]triazol-4-ylamine (16) (0.450 g, 1.2774 mmol) in anhydrous dichloromethane (15 ml), cooled to –78° C. and under a nitrogen flow, a solution of boron tribromide (2.240 g, ~0.84 ml, 8.9418 mmol) in 5 ml of anhydrous dichloromethane is added drop-wise. The mixture is allowed to reach room temperature spontaneously overnight and it is then cooled again in an ice-salt bath and the excess of the reagent is decomposed upon dropwise addition of 10 ml of methanol and 10 ml of water. After 10 min stirring, 10% sodium hydroxide solution (15 ml) is added and the aqueous layer, once separated, is acidified with 10% hydrochloric acid solution and extracted with chloroform (3×50 ml). The combined organic layers are dried over MgSO$_4$, filtered and evaporated to afford a solid residue (0.380 g, 88% yield, 99.71% pure at HPLC). M.p. 176.2-177.5° C. LC-ESI-HRMS of [M+H]+ shows 339.0854 Da. Calc. 339.086898 Da, dev. –4.4 ppm.

5-(4-Chloro-phenyl)-3-(2-fluoro-4-trifluoromethyl-phenyl)-3H-[1,2,3]triazol-4-ylamine (18)

To a stirred and ice-cooled solution of sodium methoxide (0.296 g, 5.4848 mmol) in methanol (25 ml), commercial 4-chlorobenzyl cyanide (0.610 g, 4.0222 mmol) and 1-azido-2-fluoro-4-trifluoromethyl-benzene (0.750 g, 3.6565 mmol) are added portion wise. The reaction mixture is allowed to reach room temperature spontaneously overnight, concentrated in vacuo, added water, and extracted with ethylacetate (3×80 ml). The combined organic layers are dried over MgSO$_4$, filtered and evaporated, to afford a red solid residue (1.200 g, 92% mass balance). This crude material is purified by column chromatography over silica gel (230-400 mesh) eluting with 10% ethylacetate in petroleum ether, to obtain the title compound as an off-white solid (0.350 g, 26% yield). M.p. 169.9-170.2° C. LC-ESI-HRMS of [M+H]+ shows 357.0516 Da. Calc. 357.053011 Da, dev. –4 ppm.

3-(2-Fluoro-4-trifluoromethyl-phenyl)-5-(4-trifluoromethoxy-phenyl)-3H-[1,2,3]triazol-4-ylamine (19)

To a stirred and ice-cooled solution of sodium methoxide (0.296 g, 5.4848 mmol) in methanol (25 ml), commercial 4-(trifluoromethoxy)phenylacetonitrile (0.809 g, 4.0222 mmol) and 1-azido-2-fluoro-4-trifluoromethyl-benzene (0.750 g, 3.6565 mmol) are added portion wise. The reaction mixture is allowed to reach room temperature spontaneously overnight, concentrated in vacuo, added water, and extracted with ethylacetate (3×80 ml). The combined organic layers are dried over $MgSO_4$, filtered and evaporated, to afford a brown solid residue (1.385 g, 94% mass balance). This crude material is purified by column chromatography over silica gel (230-400 mesh) eluting with 9% ethylacetate in petroleum ether, to obtain the title compound as an off-white solid (0.490 g, 33% yield). M.p. 134.2-134.9° C. LC-ESI-HRMS of [M+H]+ shows 407.0747 Da. Calc. 407.074282 Da, dev. 1 ppm.

4-[5-Amino-1-(2,4-dichloro-phenyl)-1H-[1,2,3]triazol-4-yl]-benzonitrile (20)

To a stirred and ice-cooled solution of sodium methoxide (0.388 g, 7.1802 mmol) in methanol (30 ml), 4-cyanophenylacetonitrile (0.817 g, 5.7442 mmol) and 1-azido-2,4-dichloro-benzene (0.900 g, 4.7868 mmol) are added portion wise under a nitrogen atmosphere. The reaction mixture is allowed to attain room temperature spontaneously overnight, concentrated in vacuo, added water and extracted with ethylacetate (3×100 ml). The combined organic layers are dried over $MgSO_4$, filtered and evaporated to give a dark brown gummy residue (1.425 g, 90% mass balance). This crude material is purified by column chromatography over silica gel (230-400 mesh) eluting with 20% ethylacetate in petroleum ether, to afford the title compound as a yellow solid (0.450 g, 29% yield). LC-ESI-HRMS of [M+H]+ shows 330.0319 Da. Calc. 330.031326 Da, dev. 1.7 ppm.

4-[5-Amino-1-(2-chloro-4-trifluoromethyl-phenyl)-1H-[1,2,3]triazol-4-yl]-phenol (21)

To a stirred solution of 3-(2-chloro-4-trifluoromethyl-phenyl)-5-(4-methoxy-phenyl)-3H-[1,2,3]triazol-4-ylamine (3) (1.000 g, 2.7119 mmol) in anhydrous dichloromethane (20 ml), cooled to −78° C. and under a nitrogen flow, a solution of boron tribromide (11.5497 g, ~4.36 ml, 46.1023 mmol) in 10 ml of anhydrous dichloromethane is added drop-wise. The mixture is allowed to reach room temperature spontaneously overnight and it is then cooled again in an ice-salt bath and the excess of the reagent is decomposed upon drop-wise addition of 10 ml of methanol and 10 ml of water. After 10 min stirring, 10% sodium hydroxide solution (20 ml) is added and the aqueous layer, once separated, is acidified with 10% hydrochloric acid solution and extracted with chloroform (3×70 ml). The combined organic layers are dried over $MgSO_4$, filtered and evaporated to afford a solid grey residue (0.800 g, 83% yield, 99.47% pure at HPLC). M.p. 161-162.3° C. LC-ESI-HRMS of [M+H]+ shows 355.0579 Da. Calc. 355.057348 Da, dev. 1.6 ppm.

3-(2,4-Dichloro-6-iodo-phenyl)-5-(4-methoxy-phenyl)-3H-[1,2,3]triazol-4-ylamine (22)

To a stirred and ice-cooled solution of 2-azido-1,5-dichloro-3-iodo-benzene (0.500 g, 1.5928 mmol) and 4-methoxyphenylacetonitrile (0.29 g, 1.9114 mmol) in absolute ethanol (6 ml), an ice-cooled solution of sodium methoxide (0.129 g, 2.3892 mmol) in absolute ethanol (4 ml) is added drop-wise and the mixture is allowed to reach room temperature spontaneously overnight. The resulting reaction mixture is evaporated and the gummy residue (0.740 g, 100% mass balance) is purified by column chromatography over silica gel (60-120 mesh) eluting with 0-15% ethyl acetate in hexane, to obtain the title compound as a brown solid (0.072 g, 10% yield). M.p. 72.5-73.6° C. LC-ESI-HRMS of [M+H]+ shows 460.9425 Da. Calc. 460.943317 Da, dev. −1.8 ppm.

5-(4-Chloro-2-trifluoromethyl-phenyl)-3-(4-methoxy-phenyl)-3H-[1,2,3]triazol-4-ylamine (23)

To a stirred and ice-cooled solution of 1-azido-4-methoxy-benzene (0.500 g, 3.3523 mmol) and 4-chloro-2-(trifluoromethyl)phenylacetonitrile (1.104 g, 5.0284 mmol) in absolute ethanol (15 ml), an ice-cooled solution of sodium methoxide (0.217 g, 4.0228 mmol) in absolute ethanol (8 ml) is added drop-wise. The resulting reaction mixture is evaporated and the residue is dissolved in methylene chloride and washed with water, brine, dried over $MgSO_4$, filtered and evaporated to afford ~1.25 g of crude material as brownish solid. This material is purified by crystallization from methylene chloride and petroleum ether, to obtain the title compound as brown solid (1.05 g, 83% yield). M.p. 159.2-160.2° C. LC-ESI-HRMS of [M+H]+ shows 369.0712 Da. Calc. 369.072998 Da, dev. −4.9 ppm.

5-(2,4-Difluoro-phenyl)-3-(4-methoxy-phenyl)-3H-[1,2,3]triazol-4-ylamine (24)

To a stirred and ice-cooled solution of 1-azido-4-methoxy-benzene (1.000 g, 6.7046 mmol) and 2,4-difluoro phenyl acetonitrile (1.27 g, 8.0455 mmol) in absolute ethanol (20 ml), an ice-cooled solution of sodium methoxide (0.543 g, 10.0569 mmol) in absolute ethanol (10 ml) is added drop-wise. The resulting reaction mixture is evaporated and the residue is dissolved in methylene chloride and washed with water, brine, dried over $MgSO_4$, filtered and evaporated to afford ~2 g of crude material as brownish solid. This material is purified by crystallization from methylene chloride and petroleum ether, to obtain the title compound as brown solid (1.10 g, 48% yield). M.p. 152-156.5° C. LC-ESI-HRMS of [M+H]+ shows 303.1046 Da. Calc. 303.105742 Da, dev. −3.8 ppm.

5-(2-Chloro-4-fluoro-phenyl)-3-(4-methoxy-phenyl)-3H-[1,2,3]triazol-4-ylamine (25)

To a stirred and ice-cooled solution of 1-azido-4-methoxy-benzene (1.000 g, 6.7046 mmol) and 2-chloro-4-fluoro phenyl acetonitrile (1.758 g, 10.0569 mmol) in absolute ethanol (15 ml), an ice-cooled solution of sodium methoxide (0.435 g, 8.0455 mmol) in absolute ethanol (10 ml) is added drop-wise. The resulting reaction mixture is evaporated and the residue is dissolved in methylene chloride and washed with water, brine, dried over $MgSO_4$, filtered and evaporated to afford ~2.2 g of crude material as brownish solid. This material is purified by crystallization from methylene chloride and petroleum ether, to obtain the title compound as yellowish solid (1.42 g, 66% yield). M.p. 175-176.8° C. LC-ESI-HRMS of [M+H]+ shows 319.0745 Da. Calc. 319.076192 Da, dev. −5.3 ppm.

5-(3,4-Dichloro-phenyl)-3-(4-methoxy-phenyl)-3H-[1,2,3]triazol-4-ylamine (26)

To a stirred and ice-cooled solution of 1-azido-4-methoxy-benzene (2.000 g, 13.4090 mmol) and 3,4-dichlorophenylacetonitrile (2.994 g, 16.0909 mmol) in absolute ethanol (30 ml), an ice-cooled solution of sodium methoxide (1.087 g, 20.1136 mmol) in absolute ethanol (20 ml) is added drop-wise. The resulting reaction mixture is evaporated and the residue is dissolved in methylene chloride and washed with water, brine, dried over MgSO$_4$, filtered and evaporated to afford ~4.5 g of crude material as brownish solid. This material is purified by crystallization from methylene chloride and petroleum ether, to obtain the title compound as reddish solid (1.536 g, 34% yield). M.p. 189.9-191.3° C. LC-ESI-HRMS of [M+H]+ shows 335.0483 Da. Calc. 335.046642 Da, dev. 4.9 ppm.

5-(4-Chloro-2-fluoro-phenyl)-3-(4-methoxy-phenyl)-3H-[1,2,3]triazol-4-ylamine (27)

To a stirred and ice-cooled solution of 1-azido-4-methoxy-benzene (2.000 g, 13.4090 mmol) and commercial (4-chloro-2-fluoro-phenyl)-acetonitrile (2.729 g, 16.0909 mmol) in absolute ethanol (30 ml), an ice-cooled solution of sodium methoxide (1.087 g, 20.1136 mmol) in absolute ethanol (20 ml) is added drop-wise. The resulting reaction mixture is evaporated and the residue is dissolved in methylene chloride and washed with water, brine, dried over MgSO$_4$, filtered and evaporated to afford ~4.3 g of crude material as brownish solid. This crude product is purified by column chromatography eluting with 25-35% ethyl acetate in hexane, to obtain the title compound as a yellow solid (0.140 g, 3.25% yield). M.p. 147.9-149.5° C. LC-ESI-HRMS of [M+H]+ shows 319.0779 Da. Calc. 319.076192 Da, dev. 5.4 ppm Example 2

Biological Activity

Figure 1A:
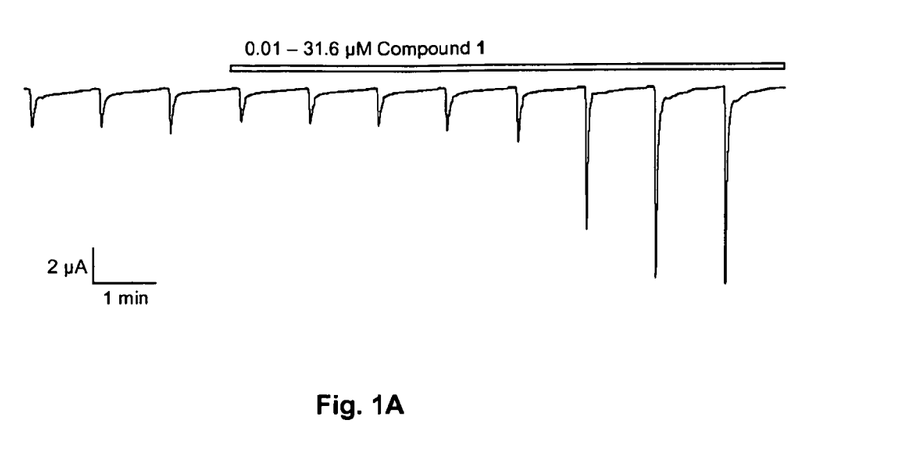
FIG. 1A shows current traces induced by 100 μM acetylcholine in the absence and in the presence of 0.01 to 31.6 μM of Compound 1.

In this example the positive modulation of wild-type nAChR α7 receptors by Compound 1 (FIGS. 1A and 1B) and Compound 3 (FIGS. 2A and 2B) was determined using nAChR α7 receptors heterologously expressed in *Xenopus laevis* oocytes.

The electrical current through the nAChR α7 channel was measured using conventional two-electrode voltage clamp and nAChR α7 currents were activated by applying pulses of agonist-containing solution onto the nAChR α7 expressing oocyte. In brief, the oocytes were placed in a recording chambers and continuously superfused with an Oocyte Ringer (OR) solution containing 90 mM NaCl, 2.5 mM KCl, 2.5 mM CaCl$_2$, 1 mM MgCl$_2$ and 5 mM HEPES (pH adjusted to 7.4). The oocytes were clamped at −60 mV and currents were induced by applying 20 s pulses of 100 μM acetylcholine dissolved in OR. The intervals between the acetylcholine applications were 5 minutes, during which the oocytes were washed with OR. The first three applications were control applications to insure a constant response level of 100 μM acetylcholine. For the subsequent 8 test applications, increasing concentrations (0.01-31.6 μM) of either Compound 1 or Compound 3 was applied 30 s before and during the acetylcholine (100 μM) application, which caused a robust increase in the acetylcholine-induced current amplitude.

Figure 1B:
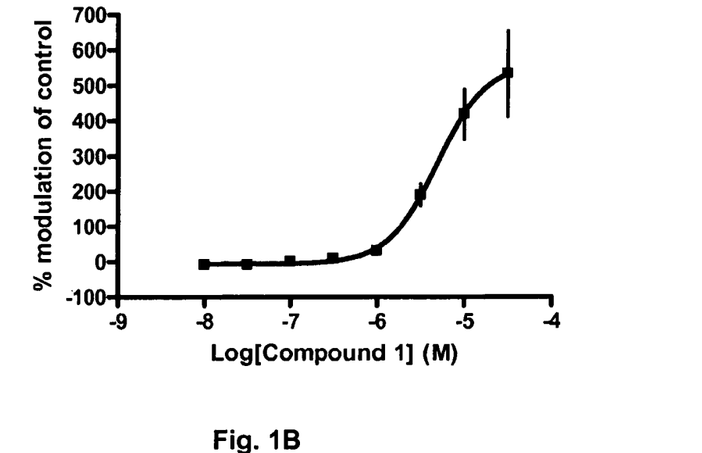
FIG. 1B shows the concentration-response relationship for the positive modulation of 100 μM acetylcholine responses induced by Compound 1; i.e. % modulation of control vs. log [c] (M). The calculated EC50-value is 4.9 μM and the maximal modulation of the acetylcholine response is 561%.
Figure 2A:
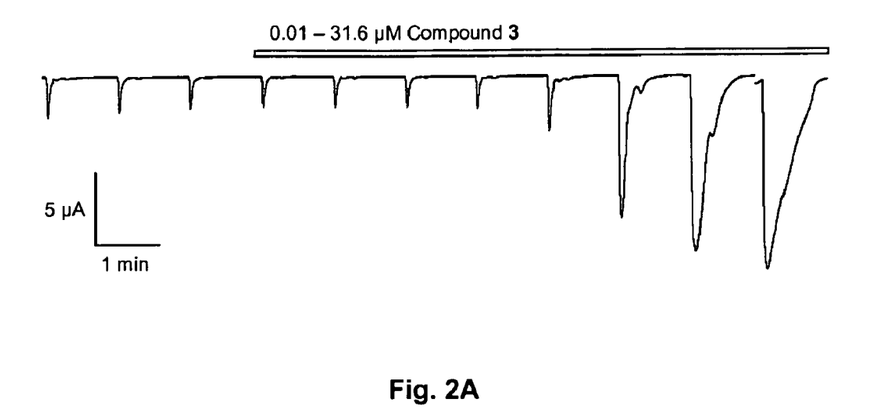
FIG. 2A shows current traces induced by 100 μM acetylcholine in the absence and in the presence of 0.01 to 31.6 μM of Compound 3.
Figure 2B:
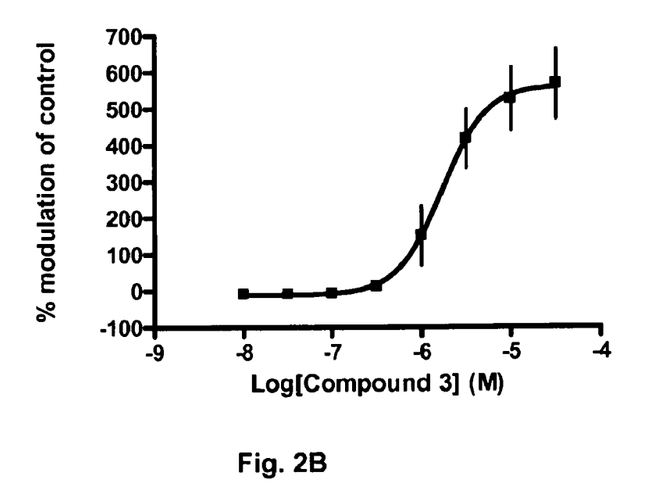
FIG. 2B shows the concentration-response relationship for the positive modulation of 100 μM acetylcholine responses induced by Compound 3; i.e. % modulation of control vs. log [c] (M). The calculated EC50-value is 1.7 μM and the maximal modulation of the acetylcholine response is 563%.

The positive modulation in the presence of Compound 1 and Compound 3 was calculated as (test-control)/control× 100% and the concentration response curve for this positive modulation was fitted to the sigmoidal logistic equation: $I = I_{max}/(1+(EC_{50}/[compound])^n)$, where $I_{max}$ represents the maximal modulation of the control response, $EC_{50}$ is the concentration causing a half maximal response, and n is the slope coefficient.

The calculated EC50 values for Compound 1 and Compound 3 are 4.9 μM and 1.7 μM, respectively, whereas the $I_{max}$-values for maximal modulation of the control responses are 561% and 563% for Compound 1 and Compound 3, respectively.

The invention claimed is:
1. A 1,2,3-triazole derivative represented by Formula I

(I)

a stereoisomer thereof or a mixture of its stereoisomers, or a pharmaceutically acceptable salt thereof, wherein
one of X' and X" represents C; and
the other of X' and X" represents N;
R' and R", independently of each other, represent hydrogen or alkyl;
one of $R^1$ $R^2$ represents hydrogen; and the other of $R^1$ and $R^2$ represents halo, trifluoromethyl, cyano, alkoxy, hydroxy, amino, N-(alkyl-carbonyl)-amino, sulfamoyl or oxadiazolyl; and
one of $R^3$ and $R^4$ represents halo; and the other of $R^3$ and $R^4$ represents trifluoromethyl;
and $R^5$ represents hydrogen; or
$R^3$, $R^4$ and $R^5$, independently of each other, represent halo or trifluoromethyl; and
Y represents an aryl or heteroaryl group selected from phenyl and isoxazolyl.
2. The 1,2,3-triazole derivative of claim 1, a stereoisomer thereof or a mixture of its stereoisomers, or a pharmaceutically acceptable salt thereof, wherein X' represents C; and X" represents N.
3. The 1,2,3-triazole derivative of claim 1, a stereoisomer thereof or a mixture of its stereoisomers, or a pharmaceutically acceptable salt thereof, wherein R' and R" both represent hydrogen.
4. The 1,2,3-triazole derivative of claim 1, a stereoisomer thereof or a mixture of its stereoisomers, or a pharmaceutically acceptable salt thereof, wherein one of $R^3$ and $R^4$ represents halo;
and the other of $R^3$ and $R^4$ represents trifluoromethyl; and $R^5$ represents hydrogen.
5. The 1,2,3-triazole derivative of claim 1, a stereoisomer thereof or a mixture of its stereoisomers, or a pharmaceutically acceptable salt thereof, wherein Y represents phenyl.
6. A 1,2,3-triazole derivative, which is
5-(5-Chloro-2-methoxy-phenyl)-3-(2-chloro-4-trifluoromethyl-phenyl)-3H-[1,2,3]triazol-4-ylamine;
3-(2-Chloro-4-trifluoromethyl-phenyl)-5-(4-methoxy-phenyl)-3H-[1,2,3]triazol-4-ylamine;
2-[5-Amino-1-(2-chloro-4-trifluoromethyl-phenyl)-1H-[1,2,3]triazol-4-yl]-4-chloro-phenol;
3-(2-Fluoro-4-trifluoromethyl-phenyl)-5-(4-[1,3,4]oxadiazol-2-yl-phenyl)-3H-[1,2,3]triazol-4-ylamine;
N-{4-[5-Amino-1-(2-fluoro-4-trifluoromethyl-phenyl)-1H-[1,2,3]triazol-4-yl]-phenyl}-acetamide;
5-(4-Amino-phenyl)-3-(2-fluoro-4-trifluoromethyl-phenyl)-3H-[1,2,3]triazol-4-ylamine;
4-[5-Amino-4-(2-fluoro-4-trifluoromethyl-phenyl)-[1,2,3]triazol-1-yl]-benzenesulfonamide;
3-(2-Fluoro-4-trifluoromethyl-phenyl)-5-(4-methoxy-phenyl)-3H-[1,2,3]triazol-4-ylamine;

4-[5-Amino-1-(2-fluoro-4-trifluoromethyl-phenyl)-1H-[1,2,3]triazol-4-yl]-phenol;
5-(2-Fluoro-4-trifluoromethyl-phenyl)-3-(4-methoxy-phenyl)-3H-[1,2,3]triazol-4-ylamine;
4-[5-Amino-4-(2-fluoro-4-trifluoromethyl-phenyl)-[1,2,3]triazol-1-yl]-phenol;
5-(4-Chloro-phenyl)-3-(2-fluoro-4-trifluoromethyl-phenyl)-3H-[1,2,3]triazol-4-ylamine;
3-(2-Fluoro-4-trifluoromethyl-phenyl)-5-(4-trifluoromethoxy-phenyl)-3H-[1,2,3]triazol-4-ylamine;
4-[5-Amino-1-(2-chloro-4-trifluoromethyl-phenyl)-1H-[1,2,3]triazol-4-yl]-phenol;
5-(4-Chloro-2-trifluoromethyl-phenyl)-3-(4-methoxy-phenyl)-3H-[1,2,3]triazol-4-ylamine;
or a pharmaceutically acceptable salt thereof.

7. A pharmaceutical composition comprising a therapeutically effective amount of a 1,2,3-triazole derivative of claim 1, a stereoisomer thereof or a mixture of its stereoisomers, or a pharmaceutically-acceptable addition salt thereof, together with at least one pharmaceutically-acceptable carrier or diluent.

8. The 1,2,3-triazole derivative of claim 1, a stereoisomer thereof or a mixture of its stereoisomers, or a pharmaceutically acceptable salt thereof, wherein X' represents N and X" represents C.

9. The 1,2,3-triazole derivative of claim 1, a stereoisomer thereof or a mixture of its stereoisomers, or a pharmaceutically acceptable salt thereof, wherein $R^3$, $R^4$ and $R^5$, independently of each other, represent halo or trifluoromethyl.

* * * * *